United States Patent [19]
van Leeuwen

[11] Patent Number: 5,851,584
[45] Date of Patent: Dec. 22, 1998

[54] METHOD FOR APPLYING A PROTECTIVE LAYER TO WHICH MICROORGANISMS DO NOT ADHERE, TO VESSELS AND UTENSILS IN THE FOOD INDUSTRY

[76] Inventor: Petrus Johannes van Leeuwen, Meer en Geerweg 9, Stompwijk, Netherlands, 2266 HW

[21] Appl. No.: 765,635

[22] PCT Filed: Jun. 30, 1995

[86] PCT No.: PCT/NL95/00239

§ 371 Date: Feb. 13, 1997

§ 102(e) Date: Feb. 13, 1997

[87] PCT Pub. No.: WO96/00505

PCT Pub. Date: Jan. 11, 1996

[30] Foreign Application Priority Data

Jun. 30, 1994 [NL] Netherlands .......................... 9401098

[51] Int. Cl.⁶ ...................................................... B05D 3/00
[52] U.S. Cl. ........................ 427/154; 427/156; 427/299; 427/353; 510/218
[58] Field of Search ..................... 427/353, 354, 427/332, 336, 154, 155, 156, 384, 299, 318, 327; 252/367.1; 424/78.09; 510/218, 514

[56] References Cited

U.S. PATENT DOCUMENTS

| | | |
|---|---|---|
| 3,941,713 | 3/1976 | Dawson et al. .......................... 427/156 |
| 3,963,635 | 6/1976 | Dawson et al. .......................... 510/467 |
| 3,963,649 | 6/1976 | Spadini et al. ........................... 252/546 |
| 4,070,452 | 1/1978 | Borchorst ................................. 510/463 |
| 4,170,241 | 10/1979 | Clapp ......................................... 134/83 |
| 4,195,077 | 3/1980 | March et al. .............................. 424/70 |
| 4,368,146 | 1/1983 | Aronson et al. ......................... 510/475 |
| 4,383,898 | 5/1983 | Renton ...................................... 427/354 |
| 4,579,676 | 4/1986 | Bull .......................................... 510/434 |
| 4,632,848 | 12/1986 | Gosset et al. ............................ 427/154 |
| 4,699,791 | 10/1987 | Tabord ................................... 424/195.1 |
| 5,211,961 | 5/1993 | Adkinson ................................. 424/616 |
| 5,306,444 | 4/1994 | Kitamura et al. ....................... 252/546 |
| 5,330,787 | 7/1994 | Berlin et al. ............................. 427/154 |
| 5,510,110 | 4/1996 | Puritch et al. ........................... 424/421 |

*Primary Examiner*—Diana Dudash
*Attorney, Agent, or Firm*—Michaelson & Wallace; Peter L. Michaelson; Edward M. Fink

[57] ABSTRACT

The present invention relates to a method for applying a protective layer to vessels or utensils used in the food industry, such as the milk and meat industries, wherein the vessels or utensils are contacted with an aqueous (natural) soap solution and then rinsed with water. The soap solution used is 2–10 ml, preferable 2–5 ml liquid soap per 100 l water, e.g. mains water. Furthermore, the relevant method is advantageously carried out at a temperature of the range of 10°–40° C. By using a soap layer as protective layer, the use of disinfectants has become superfluous in the food industry so that the attendant problem of discharging or rendering harmless harmful disinfectants foreign to nature has also been solved.

7 Claims, No Drawings

METHOD FOR APPLYING A PROTECTIVE LAYER TO WHICH MICROORGANISMS DO NOT ADHERE, TO VESSELS AND UTENSILS IN THE FOOD INDUSTRY

The present invention relates to a method for applying a protective layer to which microorganisms do not adhere, to vessels and utensils used in the food industry, such as the milk and meat industries.

As is well-known, many types of disinfectants or cleaners possessing bactericidal properties are used in the food industry. With these agents the vessels and utensils, such as cutting and mixing equipment, collecting vessels, etc., are treated in, e.g., slaughterhouses, milk plants, dairying, bakeries, and food plants of a different kind. For instance, it is known from Kirk-Othmer, Encyclopedia of Chemical Technology, 3rd edition, vol. 15, page 542, to disinfect milk equipment with a chlorine.containing solution before use. Furthermore, it is stated on page 544 of the above literature reference that alkali or chlorinated acid cleaners can be used in a "cleaning-in-place" system suitable for milk handling equipment.

It has turned out, however, that the methods known from the state of the art, in which a disinfecting liquid is used, have the drawback that after carrying out the treatment a used disinfecting liquid is obtained which normally cannot be discharged without posttreatment.

It has been found that the surface of the vessels or utensils can be kept free from microorganisms by contacting the vessels or utensils with an aqueous soap solution and then rinsing it with water.

In fact, it has turned out that the protective soap layer applied as described above possesses water-repellent properties and is reliable from a hygienic point of view so that the use of disinfectants, as has taken place until now, has become superfluous. In particular, the protective layer prevents microorganisms from adhering to the protective surface and/or growing thereon.

Besides, it is known from Australian patent application 22740/77 that monoesters of a $C_{12}$-aliphatic fatty acid and polyols possess microbicidal activity. The minimally required concentration stated is 0.001% of the monoester in a composition. It is explicitly stated that di- and triesters are useless. There is no suggestion of the formation of a layer on an object treated according to the invention described, which layer keeps the surface free from bacteria or other microorganisms.

In the method according to the invention a soap solution is used obtained by mixing 2–10 ml, preferably 2–5 ml liquid soap per 100 l water, in particular mains water. The vessels or utensils to be cleaned are then washed with the resulting soap solution, which contains a very low concentration of active agent. It is also possible to immerse the vessels or utensils in the soap solution. After this first method step the vessels or utensils are rinsed with (mains) water, after which vessels or utensils provided with a 100% hygienic soap layer are obtained. This soap layer is visible as a glossy/shiny layer and will give a fingerprint upon contact with a finger.

The above soap layer adheres to substantially all kinds of materials so that the invention also relates to vessels, etc. made of several materials.

The thickness of the soap layer applied can be reduced by starting in the preparation of the soap solution from soap blended with honey, advantageously 10–25 ml honey per 100 ml liquid soap. Microorganisms do not adhere to thus treated surfaces.

Furthermore, the soap solution to be used in the method according to the invention is advantageously prepared on the basis of liquid soap blended with ethanol, e.g. 10–25 ml ethanol per 100 ml liquid soap. With such a blended starting soap the soap solution will be prepared much more satisfactorily and rapidly than without the ethanol addition.

The vessels or utensils according to the invention can be treated within a wide temperature range of 0°–100° C., but is preferably carried out between 10° and 40° C.

The vessels or utensils should meet the requirements of being germfree or bacteria-free and clean before the treatment according to the invention. A possibility to obtain such clean vessels or utensils is to remove any deposits present with, e.g., steel wool or abrasive paper and then use a boiling soap solution or a soap solution brought to the boil during the cleaning step.

The soap to be used may be the soaps known from the state of the art, in particular those of "natural" origin, i.e. soaps prepared on the basis of products obtained from nature. On dosing grounds liquid soaps are advantageously used. For instance, in Kirk-Othmer, Encyclopedia of Chemical Technology, 3rd Edition, Vol. 21, pages 162–177, a general description of soap and soapmaking is given. More in particular, the soap used according to the invention is substantially the better soluble potassium salts of the saturated or unsaturated $C_{12-18}$ fatty acids, such as oleic acid, palmitic acid, and stearic acid. An example of such a soap is soft soap. As natural source for this soap coconut oil, palm kernel oil, talc oil, and the like may be used. In the other hand, ammonium soaps and alkanolamine soaps, such as triethanolamine soaps of coconut oil, olive oil, and the like may also be used.

With respect to the soap layer applied to the vessels or utensils it is observed that in, e.g., milk storage vessels this soap layer will not cause any change in the flavor of milk stored therein. On the contrary, the milk stored in such a storage vessel, which is free from synthetic cleaners, has a slightly richer flavor and will cream substantially faster.

Then rinse water of, e.g., a storage vessel treated with a soap solution according to the invention, which still contains a negligible amount of natural soap product, can be discharged without causing problems.

For a period of more than 10 years the applicant has been testing the above method in its business so as to apply it to milk storage vessels and milk utensils. In spite of intensive inspections for bacterial contamination and the like, made in this period by milk control stations and milk plants, no contaminated milk charges have been reported.

I claim:

1. A method for applying a protective layer to vessels or utensils used in the food industry, which protective layer prevents the adherence and/or growth of microorganisms which comprises the steps of contacting the vessels or utensils with an aqueous soap solution without disinfectant comprising from 2–10 ml of liquid soap per 100 l of water, said liquid soap comprising a potassium salt of a saturated or unsaturated $C_{12-18}$ fatty acid and rinsing the vessels or utensils with water.

2. A method in accordance with claim 1 wherein from 10–25 ml of ethanol are added per 100 ml of soap, after which the blended soap is processed with water into said soap solution which is then used to contact the vessels and/or utensils.

3. A method in accordance with claim 1 wherein the contacting and rinsing steps are carried out at 10°–40° C.

4. A method in accordance with claim 1 wherein the vessels or utensils to be treated are made germfree.

5. A method in accordance with claim 4 wherein during cleaning the vessels are washed with a boiling soap solution.

6. A method in accordance with claim 1 wherein said vessel or utensil is used for meat.

7. A method in accordance with claim 1 wherein said vessel or utensil is used for milk.

* * * * *